United States Patent [19]
Silva

[11] Patent Number: 5,352,117
[45] Date of Patent: Oct. 4, 1994

[54] METHOD AND APPARATUS FOR ATTACHING A DENTAL MODEL TO AN ARTICULATOR

[75] Inventor: Robert Silva, Lakewood, Colo.

[73] Assignee: The Silva Group, Lakewood, Colo.

[21] Appl. No.: 85,812

[22] Filed: Jul. 6, 1993

[51] Int. Cl.⁵ .............................................. A61C 19/00
[52] U.S. Cl. .......................................... 433/60; 433/34
[58] Field of Search .......................... 433/49, 60, 67, 34

[56] References Cited

U.S. PATENT DOCUMENTS

| | | | |
|---|---|---|---|
| 2,629,929 | 3/1953 | Levine et al. | 433/60 |
| 3,581,398 | 6/1971 | Thomas | 433/34 |
| 4,462,801 | 7/1984 | Lagios | 433/60 |
| 4,538,987 | 9/1985 | Weissman | 433/60 |
| 4,600,385 | 7/1986 | Lee | 433/60 |
| 4,608,016 | 8/1986 | Zeiser | 433/60 X |
| 5,129,822 | 7/1992 | Dobbs | 433/34 |

FOREIGN PATENT DOCUMENTS

| | | | |
|---|---|---|---|
| 2922045 | 12/1980 | Fed. Rep. of Germany | 433/60 |
| 2923208 | 12/1980 | Fed. Rep. of Germany | 433/60 |

*Primary Examiner*—Gene Mancene
*Assistant Examiner*—Nicholas D. Lucchesi
*Attorney, Agent, or Firm*—Gary M. Polumbus; John B. Phillips

[57] ABSTRACT

Disclosed is a system for removably supporting dental models on the upper and lower frame members of an articulator, the system including a base plate having one side adapted to support a die-stone dental replica, and an opposite side provided with shaped registration and socket structure, the system further including an adapter plate having one side adapted to be adhesively bonded to the upper or lower articulator frame-member, and the other side of each adapter plate structured for being snapped into engagement with the opposite side of the base plate to releasably hold it on the adapter plate.

18 Claims, 2 Drawing Sheets

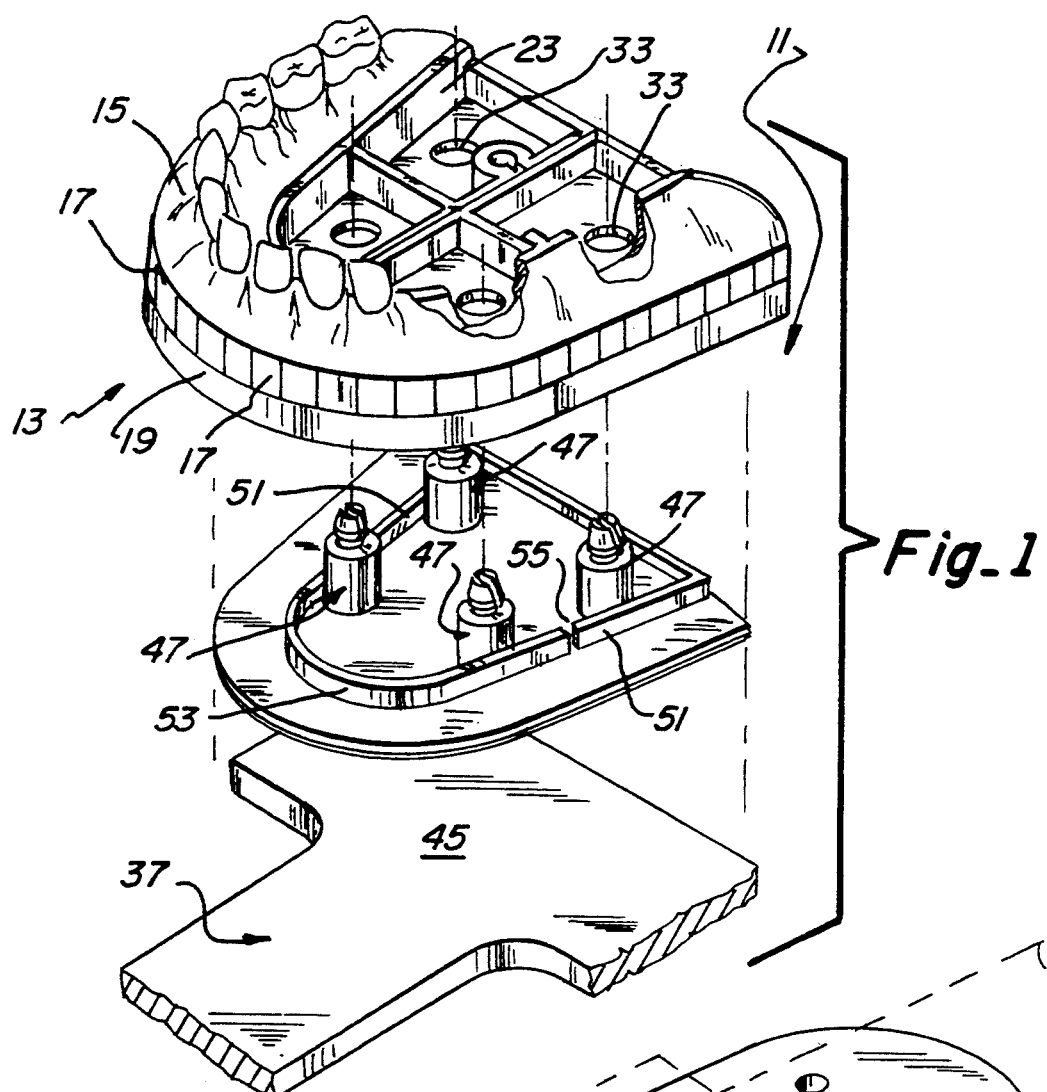
Fig_1
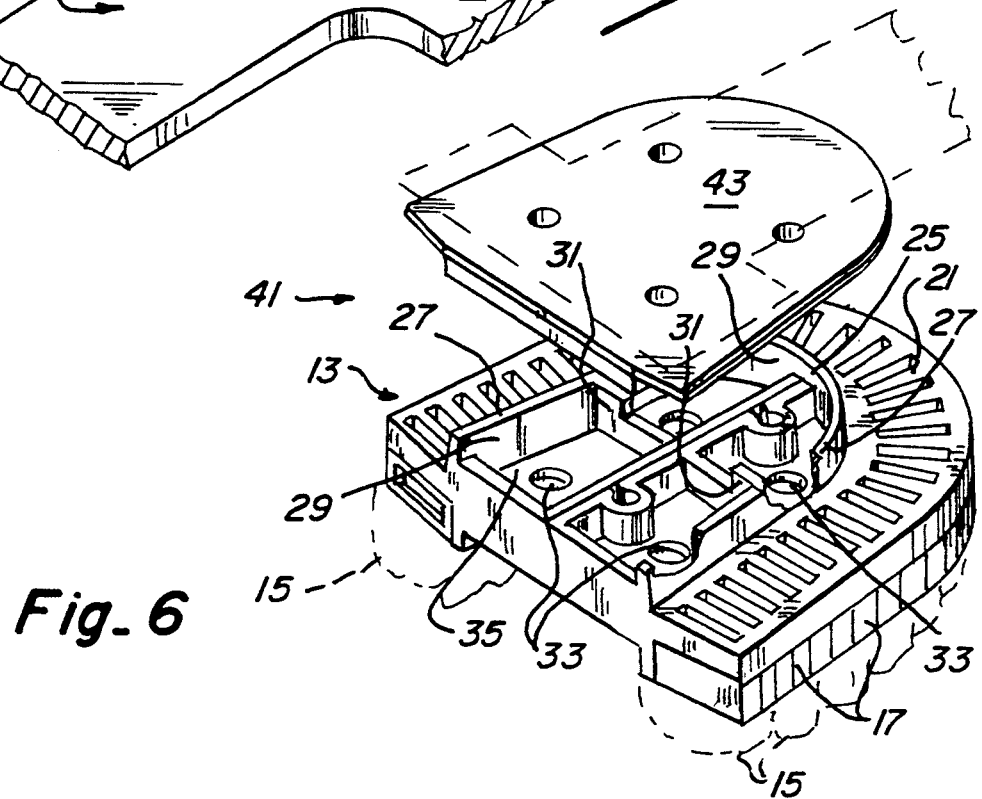
Fig_6

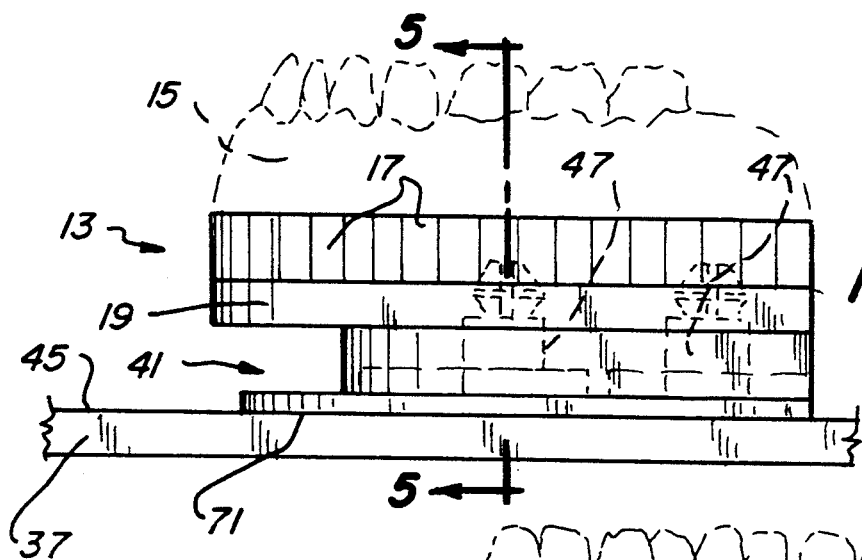
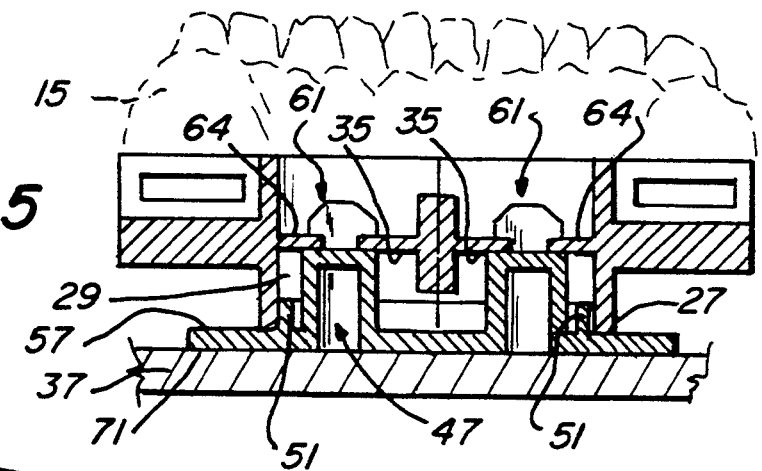
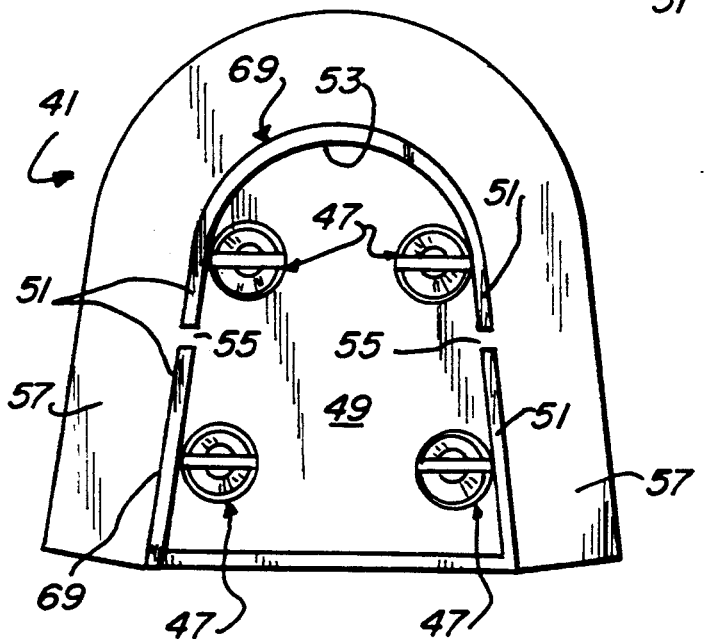
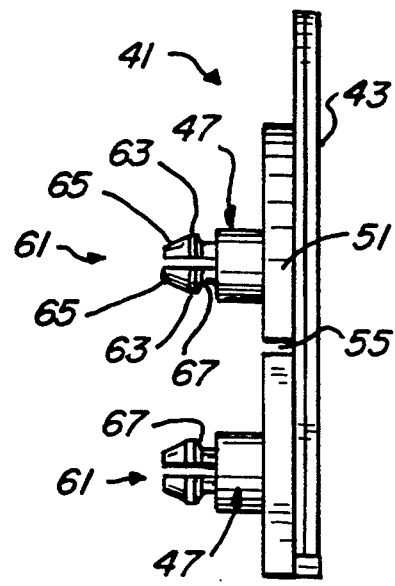

METHOD AND APPARATUS FOR ATTACHING A DENTAL MODEL TO AN ARTICULATOR

BACKGROUND OF THE INVENTION

1. Field of the Invention.

The present invention relates to systems for removably attaching a dental model to an articulator.

2. Description of the Prior Art.

In order to prepare dental plates, or inlays, crowns and bridges, die-stone or plaster dental casts are made of and then fixed in various ways in so-called articulators for further treatment. Articulators are well known in the dental industry as mechanical devices that simulate the movement of a human jaw and most often include an upper frame member spaced opposite a lower frame member, these members connected to each other for relative hinging and sliding movement. Upper and lower dental models are mounted to the upper and lower frame members respectively so that the dental models are held in relative alignment to allow precise dental measurements and relationships to be determined during the fabrication of the relevant dental prosthesis.

In earlier dental articulator systems it was required to perform the necessary processing with the dental casts remaining attached to the articulator. Because of limitations attendant to such systems, and the need to shorten dental appliance processing time, efforts ensued to develop techniques by which dental models could be removable, retractable and realignable upon an articulator. Various articulators are shown in U.S. Pat. Nos. 4,600,385, 4,923,398, and 4,245,987. The systems shown therein as well as the most widely used articulator systems can be generally characterized by the dental casts being mounted to the articulator frame by means of a mounting plate that supports a cast on one of its sides, and which mounting plate is removably attachable to the respective frame members by use of a threaded fastener. The mounting plate used is generally a flat disc-like member having a threaded hole to receive the threaded portion of a knob-equipped mounting screw which extends through the frame member to secure the mounting plate. In U.S. Pat. No. 4,923,398 a dental cast is removable from the articulator frame so that it can be worked upon effectively at other work stations and then reconnected, as required, to the articulator. In spite of the advances represented by these various prior art systems there remains a need for improvements beyond the conventional base plate and screw arrangement represented therein.

SUMMARY OF THE INVENTION

In view of the foregoing it is a general object of the present invention to provide improved means for removably attaching a dental model to an articulator.

Another object of the present invention is to provide a system that quickly, easily and simply mounts and dismounts a dental model to an articulator.

A still further object of the invention is to provide such a system in which proper alignment of the dental cast upon the articulator is maintained after repeated disconnections and reconnections.

Yet another object of the invention is to provide a system that incorporates the foregoing advantages in a reliable and economical plastic construction.

A further object of the invention is to provide a system, for removably attaching a dental model to an articulator, that can be used in conjunction with a large number of currently available articulator designs.

These, and other objects and advantages can be provided by the system of the present invention for use on an articulator having an upper frame member spaced opposite a lower frame member, for removably and reattachably mounting dental models, to the articulator frame members, the new system including a base plate having a configuration commensurate with a full upper or lower dental quadrant, with one side of the base plate being adapted to support a die-stone dental model, the other side of the base plate having fastening and alignment means including a plurality of spaced-apart vertical bores therethrough. The system includes an adapter plate that has one of its sides generally flat and adapted for being adhesively bonded to the upper or lower frame member of the articulator. The other side of adapter plate is adapted to releasably secure the dental model base plate, and has a plurality of support posts extending outwardly therefrom, the outer end of each of the posts having a outwardly facing abutment surface and resiliently depressible latching means. The latching means of each support post is adapted to be resiliently deformed and frictionally and releasably locked within a corresponding one of the vertical bores in the base plate, and the abutment surfaces will abut generally flat surfaces at the peripheries of the bores, to hold the base plate relative to the adapter plate against lateral and inward movement.

The system can further include an alignment wall on the adapter plate having slot means for receiving laterally extending alignment tongues carried on the base plate, for holding the components against relative longitudinal movement. In a preferred embodiment the system also includes laterally spaced-apart alignment walls on the adapter plate, including a curved interconnecting portion which are designed to be snugly engaged against inside surfaces of spaced-apart walls and adjoining curved wall portion on a base plate, to provide additional stability and support against relative movement of the connected components.

A greater appreciation of the invention will be obtained by resort to the detailed description, including drawings, and the claims which follow.

BRIEF DESCRIPTION OF THE DRAWINGS

FIG. 1 is a fragmented, exploded perspective view illustrating a mounting system according to the present invention;

FIG. 2 is a top plan view of an adapter plate used in the present invention;

FIG. 3 is a side elevational view of the adapter plate of FIG. 2;

FIG. 4 is a side elevational view showing a dental model supported on an articulator using the present invention;

FIG. 5 is a sectional view taken along the line 5—5 of FIG. 4 and;

FIG. 6 is a perspective view, with parts broken away for the sake of clarity, of a system according to the present invention.

DETAILED DESCRIPTION OF THE INVENTION

Referring now to the drawings, FIG. 1 indicates by reference numeral 11 a preferred embodiment, according to the present invention, of a system for mounting a dental model to an articulator. The system includes a base plate assembly 13 which supports on one face as shown, a die-stone dental model 15. Base plate assembly 13 is preferably of a unique advantageous plastic modular construction that can support a full upper or lower bilateral dental replica such as dental model 15 which is directly molded to a plurality of mounting blocks 17 that are releasably secured to an upper surface of a base plate 19. Such apparatus for supporting a dental model is described in detail in U.S. Pat. No. 5,197,874 which disclosure is incorporated herein by reference. It will be seen that the base plate assembly 13, while still capable of carrying out the invention of U.S. Pat. No. 5,197,874, has been uniquely adapted to serve the attachment system that is being described herein. Thus as FIGS. 1 and 6 best show, the base plate assembly 13 includes a base plate flange 21 for supporting the mounting blocks 17, and has spaced-apart walls 23 that are interconnected by a curved wall portion 25, which walls combine to provide a continuous upper edge 27. It is also seen that walls 23 and 25 provide upright, vertical inside surfaces 29. Finally it is noted that there are a pair of transverse alignment tongues 31, and that circular bores 33 are provided through the horizontal walls 35 of the base plate 19.

Although FIGS. 1 and 4 illustrate the system of the invention in conjunction with a lower articulator frame member 37, it is to be understood that the attachment system described will be equally applicable to an upper articulator frame member.

The system of the invention also features an adapter plate 41, also constructed of a suitable durable plastic material by conventional molding techniques of the plastics industry, and it has a back wall with a generally flat surface 43 which can be given a deliberate textured or roughened configuration in order to enhance its application in what is known in the art as hot-melt adhesive bonding. In this regard it is noted here that the system of the invention is advantageously made available for use with a large variety of existing articulators, since all that is necessary on such articulators is an outward surface on frame member, such as surface 45 in FIG. 1, that is sufficiently large to provide a bonding surface for a suitable hot melt adhesive.

FIGS. 1, 2 and 3 show that the other side of adapter plate 41 is characterized by four mounting posts 47 extending outwardly from surface 49, a pair of holding walls 51 including an interconnecting arcuate wall portion 53, transverse slots 55 in the walls 51, and finally a flat flange surface 57 extending from the perimeter of the walls 51 and 53 as shown. FIG. 3 best shows that the outer end of each mounting post 47 has a flat, annular abutment surface 59, from which surface extends a bifurcated latching tab 61 comprising a pair of spaced-apart latch elements 63 which are resiliently deformable towards each other. Note that each element 63 has an inclined upper surface 65 and a lower, under-surface 67, and each tab 61 is adapted to be snapped into releasable locking engagement within a base plate bore 33. The latching tab 61 ordinarily having a larger diameter than that of a bore 33 however when tab 61 is pushed into a bore 33 the resulting sliding contact with the sloped surfaces 65 results in a camming action that pushes the elements 63 towards each other to reduce the effective diameter of tab 61 sufficiently to allow full insertion of tab 61. The outer annular surface 59 of a post 47 is designed to abut the flat surface of walls 35 at the perimeter of a hole 33, and lower surfaces 67 are adapted to engage the other side of a hole 33, that is, the base plate surface 64, shown in FIG. 5. The resilient elements 63 will spring back substantially to their original spaced-apart configuration when the tab 61 is fully inserted in a bore 33, and the lower surfaces 67 have slopes sufficient to result in the frictional engagement required to firmly hold a base plate, yet sufficient to cam the elements 63 towards each other when a tab 61 is deliberately pulled from a bore 33 during removal of a base plate 13 from an adapter plate 41 in a manner to be described hereinafter.

It is further noted that in the preferred embodiment of the invention that the walls 51 and 53 of adapter plate 41 provide outer surfaces 69 that are adapted to conform to and be fit snugly into engagement with the inside wall surfaces 29 of a base plate as FIG. 5 illustrates. It is also to be noted that the two slots 55 of base plate 41 are designed to receive the laterally extending alignment tongues 31 of a base plate 19.

A further noteworthy aspect of this preferred embodiment of the invention is that the flange surface 57 of adapter plate 41 is adapted, when a base plate is mounted to an adapter plate 41, to make flush abutting engagement with the upper edge 27 of the base plate walls 23 and 25 so as to additionally stabilize the base plate on the adapter plate 41.

In using the attachment system according to the invention a suitable conventional hot-melt adhesive is first applied to the surface of an articulator frame such as lower frame member 37. FIG. 4 shows an adhesive layer 71 between articulator frame surface 45 and adapter plate 41. After being properly oriented and located on the frame member 37 an adapter plate 41 can thusly be secured in place. A dental base plate can then be quickly and conveniently mounted to the adaptor plate 41. This can be accomplished by aligning the mounting posts 47 with corresponding bores 33 of the base plate 19, and then pressing the latching tabs 61 simultaneously into bores 33. The fully inserted elements 63 will snap in place such that the posts' annular surfaces 59 will abut the surface 35 of the base plate to stabilize the base plate against relative inward movement to the adapter plate.

Thus the base plate 19 is secured against movement from the adaptor plate with sufficient holding force to meet the ordinary requirements of model processing on an articulator, while at the same time allowing the components to be disconnected by pulling them apart by hand when required. Engagement of the posts in bores 33 also serves to hold the base plate against relative lateral movement. Finally it is noted that the alignment tongues 31 engage the two slots 55 in the adapter plate to additionally secure the mounting plate against relative longitudinal movement. The engagement of the outside wall surface 69 snuggly against the base plate wall surfaces 29 will further register the base plate on the adapter plate and hold the base plate against relative twisting movement.

While the preferred embodiment has been described herein it should be appreciated that other variations of the invention will be apparent to a person skilled in the art after reading the foregoing disclosure. Accordingly, it is intended that the invention include all such modifications and alterations as fall within the true scope and breath of the invention as defined in the claims which follow.

What is claimed is:

1. System for removably mounting a dental model to an articulator that includes a pair of upper and lower opposed frame members, said system including:
   a. a base plate having a configuration commensurate with at least one quadrant of a person's dental structure, wherein a bottom side of said base plate includes a plurality of spaced apart apertures, and wherein a top side of said base plate is adapted to be selectively attached to and detached from the dental model so that at least one segment of the dental model is selectively detachable and replaceable with respect to the base plate; and
   b. an adapter plate having a bottom side that is adapted for being secured to one of said upper or lower frame members, and a top side having a plurality of spaced support posts for engagement with the corresponding base plate apertures to releasably attach the adapter plate to the base plate.

2. System as defined in claim 1 wherein each said support post includes a resiliently deformable latching tip for making latching engagement with a respective aperture.

3. System as defined in claim 2 wherein said latching tips are adapted to be snapped into releasable frictional holding engagement with said apertures.

4. System as defined in claim 2 wherein each of said support posts has an outer end and a shelf on said outer end that is adapted to abut said base plate at a periphery of the respective aperture to hold said base plate against movement towards said adapter plate.

5. System as defined in claim 2 wherein said resiliently deformable latching tips are adapted to be slidably snapped into engagement with said apertures, and slidably disengaged from said apertures.

6. System as defined in claim 1 wherein:
   the top side of the adapter plate further includes a wall circumscribing the plurality of support posts, said adapter plate wall including spaced-apart substantially straight portions and a curved portion interconnecting said substantially straight portions, and said adapter plate wall further having an outside surface; and
   the bottom side of the base plate further includes a wall circumscribing the plurality of apertures, said base plate wall including spaced-apart substantially straight portions and a curved portion interconnecting said substantially straight portions, and said base plate wall further having an inside surface that is engagable by the outside surface of the adapter plate wall to hold said base plate against lateral movement relative to said adapter plate.

7. System as defined in claim 6 wherein said base plate wall further includes an outer edge adapted to abut said adapter plate to hold said base plate against inward movement relative to said adapter plate.

8. System as defined in claim 6 wherein there is at least one vertical slot in the substantially straight adapter plate wall portions and wherein said base plate further includes a transverse wall portion adapted to engage said slot to hold said base plate against forward or rearward movement relative to said adapter plate.

9. System as defined in claim 6 wherein said adapter plate has a flange-like portion extending laterally from the adapter plate wall and whereby when said base plate is mounted to said adapter plate there is a substantial finger-engagable vertical spacing between said flange-like portion and said base plate.

10. System as defined in claim 1 wherein an adhesive is used to secure the adapter plate to the articulator, and the bottom side of said adapter plate is textured to enhance an adhesive seal between the adapter plate and the respective articulator frame member.

11. System as defined in claim 1 wherein said base plate and adapter plate are constructed of a polymeric material.

12. System for removably mounting a dental model to an articulator that includes a pair of upper and lower opposed frame members, said system comprising:
   a base plate having a configuration commensurate with at least one quadrant of a person's dental structure, the base plate including a central portion and an arcuate flange portion extending laterally from the central portion, wherein a bottom side of the central portion includes a plurality of spaced apart apertures, and wherein a top side of the arcuate flange portion is adapted for releasable attachment to the dental model so that at least one segment of the dental model may be selectively detachable and replaced with respect to the arcuate flange portion; and
   an adapter plate having bottom side that is adapted for being secured to one of either said upper or said lower frame members of the articulator, and a top side having a plurality of spaced support posts for making latching engagement with the respective apertures in the central portion of the base plate to releasably attach the adapter plate to the base plate.

13. System as defined in claim 12, wherein the adapter plate includes a central section containing the plurality of support posts and a flange extending laterally from the central section, and wherein a finger-engagable space is formed between the arcuate flange portion of the base plate and the flange of the adapter plate when the base plate and the adapter plate are attached.

14. System as defined in claim 13, wherein each support post includes a resiliently deformable latching tip adapted to be snapped into releasable frictional engagement with a respective aperture.

15. System as defined in claim 14, wherein each latching tip is attached to a flat abutment surface on the respective support post, said abutment surface adapted to abut the base plate at a periphery of the respective aperture and maintain the finger-engagable space between the flange portion of the base plate and the flange of the adapter plate when the base plate and the adapter plate are attached.

16. System as defined in claim 14 wherein:
   the top side of the adapter plate further includes a wall bordering the central section of the adapter plate, said adapter plate wall having an outside surface; and
   the bottom side of the base plate further includes a wall bordering the central portion of the base plate, said base plate wall having an inside surface that is engagable by the outside surface of the adapter plate wall to prevent lateral movement between the base plate and the adapter plate when the base plate is attached to the adapter plate.

17. System as defined in claim 16 wherein the base plate wall further includes an outer edge adapted to abut the flange of the adapter plate adjacent the adapter plate wall to maintain the finger-engagable space between the flange portion of the base plate and the flange of the adapter plate when the base plate and the adapter plate are attached.

18. System for releasably attaching a dental model to an articulator that includes a pair of upper and lower opposed frame members, said system comprising:

a base plate having a configuration commensurate with at least one quadrant of a person's dental structure, the base plate including a central portion and an arcuate flange portion extending laterally from the central portion, wherein a bottom side of the central portion includes a plurality of spaced apart apertures, and wherein a top side of the arcuate flange portion is adapted for supporting the dental model; and an adapter plate having a bottom side that is adapted for being secured to one of either said upper or said lower frame members of the articulator, and a top side having a central section and a flange extending laterally from the central section, the central section having a plurality of spaced support posts for making latching engagement with the respective apertures in the central portion of the base plate to releasably attach the adapter plate to the base plate with a finger-engagable space between the arcuate flange portion of the base plate and the flange of the adapter plate.

* * * * *